United States Patent
Howe et al.

[11] Patent Number: 5,088,834
[45] Date of Patent: Feb. 18, 1992

[54] UNITARY PROBE COVER

[75] Inventors: Randall R. Howe, Greeley, Colo.; Joseph P. Brown, Valley Center, Calif.

[73] Assignee: Thermoscan Inc., Tucker, Ga.

[21] Appl. No.: 752,932

[22] Filed: Aug. 30, 1991

Related U.S. Application Data

[63] Continuation of Ser. No. 573,382, Aug. 24, 1990, abandoned.

[51] Int. Cl.$^5$ .............................................. G01K 1/08
[52] U.S. Cl. .............................. 374/158; 374/209; 128/664; 128/736
[58] Field of Search ............... 374/209, 158; 128/736, 128/664; 206/306

[56] References Cited

U.S. PATENT DOCUMENTS

| | | | |
|---|---|---|---|
| 738,960 | 9/1903 | Vaughan et al. | 374/209 |
| 1,363,259 | 12/1920 | Mills | 374/209 |
| 3,673,868 | 7/1972 | Beury, III et al. | 374/158 |
| 3,703,892 | 11/1972 | Meyers | 374/158 |
| 3,833,115 | 9/1974 | Schapker | 374/209 |
| 3,880,282 | 4/1975 | Naumann | 374/209 |
| 3,949,740 | 4/1976 | Twentier | 374/158 |
| 4,054,057 | 10/1977 | Kluge | 374/158 |
| 4,159,766 | 7/1979 | Kluge | 374/209 |
| 4,588,306 | 5/1986 | Burger et al. | 374/158 |
| 4,662,360 | 5/1987 | O'Hara et al. | 374/158 |
| 4,784,149 | 11/1988 | Berman et al. | 374/158 |
| 4,790,324 | 12/1988 | O'Hara et al. | 374/158 |
| 4,797,840 | 1/1989 | Fraden | 128/736 |
| 4,911,559 | 3/1990 | Meyst | 374/158 |
| 5,018,872 | 5/1991 | Suszynski et al. | 374/158 |

*Primary Examiner*—William A. Cuchlinski, Jr.
*Assistant Examiner*—Diego F. F. Gutierrez
*Attorney, Agent, or Firm*—Hugh H. Drake

[57] ABSTRACT

A unitary probe cover for an infrared radiation thermometer has a frustum-shaped sheath which fits over the thermometer probe. A base, which is engageable with the probe, is formed integrally with and around the periphery of the proximal end of the sheath to hold the sheath over the probe. The sheath is made of an infrared transparent material and is formed to have a thinner distal end portion terminating in a thin window which passes infrared radiation through the probe into the thermometer.

14 Claims, 2 Drawing Sheets

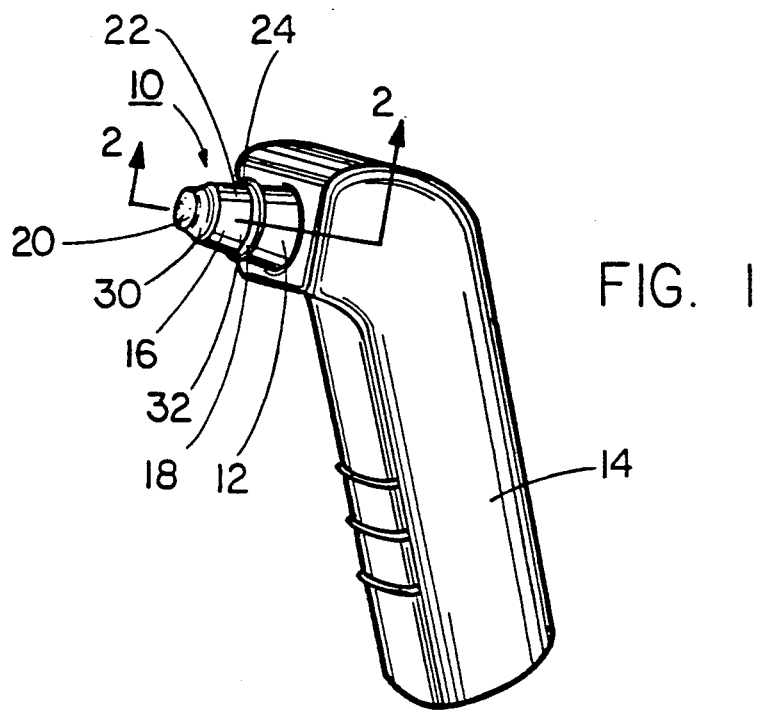
FIG. 1
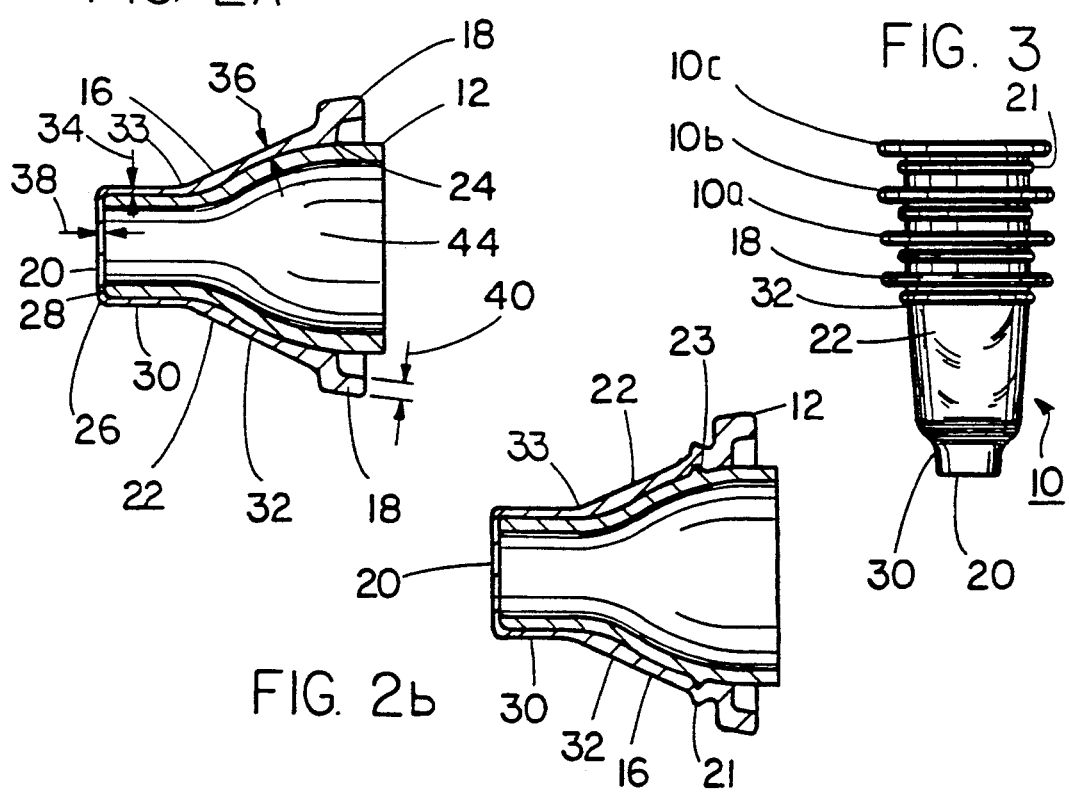
FIG. 2A
FIG. 2b
FIG. 3

UNITARY PROBE COVER

This is a continuation of copending application Ser. No. 07/573,382, filed on Aug. 24, 1990, now abandoned.

FIELD OF INVENTION

The present invention relates generally to probe covers. More particularly, the present invention pertains to sanitary covers for the probes or specula of medical instruments. The present invention is particularly, but not exclusively, useful as a sanitary cover for the probe of a thermometer which measures temperatures of the human body by detecting and analyzing infrared (IR) radiation from a surface of the body, such as in the ear canal.

BACKGROUND OF THE INVENTION

It is well known that an accurate reading of the temperature of a human body is helpful, if not essential, for the diagnosis and monitoring of numerous ailments. Indeed, several types of thermometers have been developed for these purposes. For instance, one type of reusable thermometer which is being increasingly used is the infrared radiation (IR) thermometer. An exemplary such device is disclosed in U.S. Pat. No. 4,797,840 to Fraden.

Importantly, as with the other types of thermometers, it is necessary that there be a sanitary contact between the IR thermometer and the body during operational use. It is well known that such a sanitary contact can be accomplished in several ways. For example, the thermometer may either be sterilizable prior to a subsequent use, or used only once and then discarded. Additionally, the thermometer may somehow be protected from contact with the body. For IR thermometers which cannot be easily sterilized or are too expensive to be simply thrown away the only practical way to insure subsequent sanitary uses of the thermometer may be to provide a disposable cover or barrier for that part of the thermometer which comes into contact with the body.

Typically, in order to determine the temperature of a human body, IR thermometers use a hollow probe, or speculum, to establish a radiation pathway between a selected body surface and the thermal radiation detecting element of the thermometer. It is this probe which is normally inserted into the ear canal of the patient or otherwise brought into contact with a body surface. Thus, it is the probe of an IR thermometer which needs to be protected from contamination.

Several probe covers have been suggested to accomplish the purpose of providing a sanitary barrier between a patient and the probe of a thermometer. In addition to the sanitary barrier function, these devices typically must also fulfill up to three additional functions. First, the probe cover must typically be transparent to radiation having a wavelength in the far infrared range, i.e. at least part of the probe cover must function as an infrared window. Also, the probe cover must securely attach to the thermometer housing, and it should provide for the easy and comfortable insertion of the probe into a body cavity (e.g. the ear canal).

Previous probe covers have typically used separate components to meet all four requirements, or have not fully met one or more of these requirements. As an example of a probe cover which joins separate components to perform the various probe cover functions discussed above, U.S. Pat. No. 4,662,360 to O'Hara et al. discloses a sanitary protective cover for the ear canal probe of a tympanic thermometer. The O'Hara device, as disclosed, is a multi-part cover which incorporates an essentially rigid side wall that serves as a speculum. One part (the film) of the O'Hara device is used as the infrared window and the other part (the tube) of the O'Hara device is used to fulfill the other three requirements discussed above.

Similarly, U.S. Pat. No. 4,911,559 to Meyst, et al. discloses a three-piece probe cover that has a stretchable film which serves as a sanitary barrier, an infrared window and a probe (speculum) envelope to facilitate insertion of the probe into the ear. The device has a separate rigid ring for securely fitting the probe cover onto the probe.

Still another probe cover is disclosed in U.S. Pat. No. 4,790,324 to O'Hara. It has a tubular body much thicker than a window transparent to infrared radiation and disposed across the outer end of the body. The inner tube end surrounds but is spaced from the probe.

Unfortunately, such multi-part covers require the accomplishment of numerous tasks during the manufacturing procedure. Additionally, when the various parts of a multi-part probe cover are assembled, seams are created along the boundaries of the interconnected parts which, if they protrude excessively from the probe cover, can be uncomfortable for the patient. Perhaps more importantly, the integrity, and therefore the sanitary efficacy, of the Probe cover is likely to be more easily compromised along a seam than in the other surface areas of the cover.

Thus, it is desirable that the probe cover be of unitary construction. One such probe cover is disclosed in U.S. Pat. No. 3,949,740 to Twentier. The Twentier patent discloses a rigid probe cover which covers all but the distal end of the probe. Thus, the Twentier probe establishes an infrared window for its associated probe by not covering the distal end of the probe at all. Unfortunately, because the Twentier device does not cover the distal end of the probe, the distal end may potentially become contaminated during use. Accordingly, there is still a need to provide a unitary probe cover which covers substantially all of the probe of a thermometer to establish an effective sanitary barrier.

The present invention recognizes that an effective unitary probe cover for an IR thermometer can be produced without requiring the assembly of various probe cover parts during the manufacturing process. Further, the present invention recognizes that a sanitary probe cover need not function as a speculum in order to accomplish its protective function. Accordingly, it is an object of the present invention to provide a probe cover which is of unitary construction. Still another object of the present invention to provide a probe cover which establishes a continuous integrally formed unitary barrier between the probe and the surface of the body which would otherwise come into contact with the probe. Finally it is an object of the present invention to provide a probe cover that is relatively easy to use and cost-effective to manufacture.

SUMMARY OF THE INVENTION

The preferred embodiment of a probe cover for an IR thermometer in accordance with the present invention includes a substantially hollow, frustum-shaped sheath having an open end and a closed end. The sheath is made from a single unitary piece of infrared transparent film which is sufficiently thin at the closed end of the sheath to establish a infrared window. The open end of the sheath is defined by its periphery, i.e. the edge of the piece of film. As indicated, the sheath has a frustum-shaped wall that connects the open end of the sheath with the closed end and effectively defines the shape of the sheath. The thickness of the wall may be either uniform or tapered from a relatively thick configuration at the open end of the sheath to a relatively thin configuration near the closed end of the sheath.

A ring-shaped base is integrally formed around and projects outwardly from the periphery of the open or proximal end of the sheath and is dimensioned to surroundingly engage and thereby establish an interference or interlocking fit with the outside of the hollow probe of an IR thermometer when the cover is placed over the probe. Importantly, when the base of the probe cover is engaged with the thermometer, the sheath effectively surrounds the probe and the infrared window of the sheath is positioned over the distal or free end of the probe. Thus, the window is disposed over, or across, an open pathway which extends through the probe and along which infrared radiation from inside the ear canal can be transmitted to the thermal detecting elements of the thermometer. In the construction of the unitary probe cover, both the base and the proximal portion of the wall of the sheath are relatively thick and rigid, while the IR window and the adjacent distal portion of the wall of the sheath are relatively thin and essentially flaccid. Preferably, the entire probe cover is made of a polymer, such as polyethylene or polypropylene.

The features of the present invention which are believed to be patentable are set forth with particularity in the appended claims. The organization and manner of operation of two specific embodiments of the invention, together with further objects and advantages thereof, may best be understood by reference to the following description taken in connection with the accompanying drawings, in the several figures of which like reference numerals identify like elements, and in which:

BRIEF DESCRIPTION OF THE DRAWINGS

FIG. 1 is a perspective view of an IR thermometer with the probe cover of the present invention engaged to cover the probe of the thermometer;

FIG. 2A is a cross-sectional view of the probe cover engaged with a portion of the thermometer probe as seen along the line 2—2 in FIG. 1;

FIG. 2B is a cross-sectional view of an alternate embodiment of the probe cover of the present invention showing the formation of a snap ring, as would be seen along the line 2—2 in FIG. 1;

FIG. 3 is an elevational view of a plurality of nested probe covers;

DESCRIPTION OF THE PREFERRED EMBODIMENT

Figure 4A:
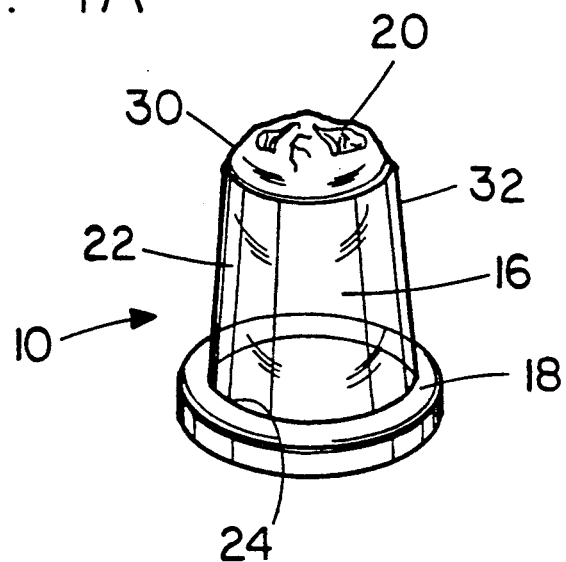
FIG. 4A is an isometric view of the probe cover of the present invention shown in FIG. 2A.

Referring initially to FIG. 1, the probe cover according to the present invention is generally designated 10 and is shown positioned over the hollow probe 12 of an IR thermometer 14. In this instance, probe 12 is in the form of a speculum shaped and sized for insertion within the ear canal. Cover 10 includes a hollow sheath 16 that is unitarily formed with a stiff radially-thicker circular base ring 18 at one end adjacent or approximate to thermometer 14. More specifically, sheath 16 and base ring 18 are formed from a single piece of material which does not readily absorb light having wavelengths in the far infrared range (approximately four to twenty microns). Polyethelyne or polypropylene (for instance, polyolefin or a suitable co-polymer are preferred). When sheath 16 is positioned on probe 12 the distal or closed end of sheath 16 forms a flat, generally circular, wrinkle-free infrared transparent window 20. Also as shown in FIGS. 2A and 4A, wall 22 of sheath 16 is shaped as a right circular frustum that extends between window 20 and the periphery 24 of base ring 18.

Several embodiments of the probe cover are contemplated by the present invention and two of them are described in detail. First as seen in FIGS. 2A and 4A the preferred embodiment of the present invention has a substantially rigid base ring 18 which is dimensioned for surrounding engagement with probe 12. More particularly, base ring 18 establishes a secure fit on probe 12. With this fit, ring 18 holds cover 10 on probe 12 so that window 20 of sheath 16 is positioned and stretched directly across the distal opening 26 of probe tip 28.

The radial thickness of base ring 18 may vary from fifteen thousandths (0.015) to fifty thousandths (0.050) of an inch depending on the particular application of probe 12, while window 20 has a thickness of between 0.001 and 0.0005 inch when using one of the materials mentioned above. The thickness is selected to be as thin as possible to minimize attenuation of the radiation while yet remaining sufficiently strong to resist being torn or distorted during use. Also, as shown, wall 22 of sheath 16 extends between window 20 and base ring 18 to cover a substantial portion of the probe 12. Wall 22 is virtually a continuation of ring 18 and its thickness in this case is established to be between five ten thousandths (0.0005) and thirty thousandths (0.030) of an inch. To provide additional stiffness to wall 22, several elongated ribs (not shown) may be formed along wall 22.

Figure 4B:
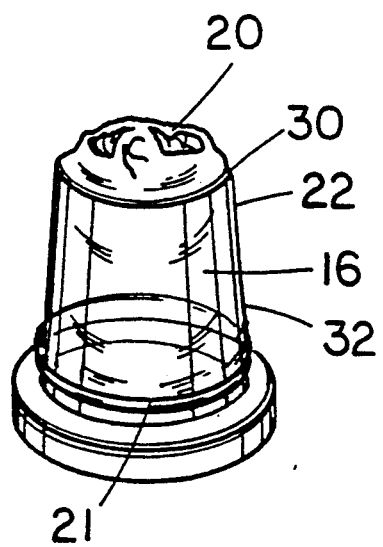
FIG. 4B is a isometric view of the alternate embodiment of the probe cover of the present invention shown in FIG. 2B.

Alternatively, as shown in FIGS. 2B and 4B, wall 22 of sheath 16 is formed to include a offset 21 that defines an internal circular recess and an external circular rib to enable base ring 18 to function as a snap ring. Offset 21 circumscribes wall 22 and is dimensioned to surroundingly engage probe 12. More specifically, the recess of offset 21 forms an interlocking fit with a circular nipple 23 formed on probe 12. Nipple 23 may be in the form of a plurality of protrusions which are raised on probe 12 or a continuous raised ring which circumscribes probe 12.

In either embodiment, wall 22 includes, in axial order from window 20 to periphery 24, a distal portion 30 and a proximal portion 32. The shape of proximal portion 32 of wall 22 is adapted for comfortable insertion into a body cavity, such as an auditory canal. As disclosed above, window 20 has a thickness 38 of between approximately one thousandth (0.001) and five ten thousandths (0.0005) of an inch. Consequently, window 20 is sufficiently thin to be effectively infrared transparent. Additionally, distal portion 30 of wall 22 has a thickness 34 which is also between approximately one thousandth (0.001) and five ten thousandths (0.0005) of an inch. The proximal portion 32 of wall 22, on the other hand, has a thickness 36 which is approximately twenty thousandths (0.020) of an inch.

In the preferred form, wall 22 is gradually tapered from approximately twenty thousandths (0.020) of an inch in proximal portion 32 to a thickness of approximately five ten thousandths (0.0005) of an inch in distal portion 30. However, proximal portion 32 of wall 22 can have a thickness as great as thirty thousandths (0.030) of an inch. Accordingly, the relatively thick base 18 and the relatively thick proximal portion 32 of wall 22 are both substantially stiffer than window 20 and distal portion 30 of wall 22, both of which are relatively thinner and substantially flaccid. Preferably, the length of the tapered portion 33 of wall 22 is at least ten times the difference between the thickness 36 of proximal portion 32 and the thickness 34 of distal portion 30. This gradual tapering has several advantages, such as better tear-resistance, better patient comfort and ease of manufacturing.

In another embodiment, wall 22 can be effectively stiffened along most of its length by being made to have a substantially uniform thickness (e.g. 0.020 in). With a stiff wall 22, cover 10 may also be useful as a speculum. In either case, the thickness 40 of base ring 18 and thickness 36 of proximal portion 32 are sufficient to provide a structural stiffness for securely attaching cover 10 to probe 12. The thickness of window 20, however, remains approximately five to ten thousandths (0.0005–0.0010) of an inch to establish an IR transparent window. In a further alternative, the entire length of wall 22 is made to be flaccid, i.e. wall 22 would have a thickness of five ten thousandths (0.0005) of an inch or greater from base ring 18 to window 20.

Because of the varying thickness of the material of probe cover 10, the general frustum shape of probe cover 10 is established and maintained by proximal portion 32, while the substantially circular shape of periphery 24 is established and maintained by base ring 18. On the other hand, because window 20 and distal portion 30 are effectively flaccid for the preferred embodiment of cover 10 they can readily conform to the contour of probe 12 when cover 10 is fitted over the probe. Indeed, when cover 10 is properly positioned over probe 12, window 20 and distal portion 30 of wall 22 are drawn tightly against the outer surface of probe 12 to create a sanitary barrier over the probe 12. Importantly, window 20 and distal portion 30 of the cover 10 are substantially wrinkle-free when the cover 10 is properly positioned over probe 12.

The inclusion of thin distal portion 30 ensures that a thin, transparent portion of sheath 16 is positioned to serve as window 20 even should cover 10 somehow be mounted askew. Distal portion 30 also enables cover 10 to fit various probes or specula of differing distal portion diameter or length. At the same time, manufacturing tolerances may be relaxed. As intended for the present invention and as indicated above, the entire cover 10, including base ring 18, window 20, and wall 22, is made from a single continuous piece of material. As indicated above, this material is a material such as polyethylene or polypropylene (for instance, polyolefin or a suitable co-polymer are preferred. Regardless of the particular material used for the manufacture of cover 10, however, it is important that the window 20 be sufficiently thin to be effectively transparent to the transmission of infrared energy. Further, in order to obtain consistent results and minimize any attenuation of the infrared radiation which will pass through window 20, window 20 should preferably be as flat and wrinkle-free as possible when fitted onto probe 12, as disclosed above.

Referring for the moment to FIG. 3, a method for the storage of several probe covers 10, respectively designated 10a, 10b and 10c, is shown. Specifically, because of the dimensions of wall 22 of sheath 16, the probe covers 10, 10a, 10b, 10c, can be nested, as shown for the purpose of space saving.

OPERATION

First, probe cover 10 is engaged with probe 12. More particularly, for the embodiment shown in FIGS. 2A and 4A, base ring 18 or the substantially stiff proximal portion 32 of wall 22, or both, engage probe 12 to form an interference or friction fit with probe 12. On the other hand, for the embodiment shown in FIGS. 2B and 4B, the recess of offset 21 engages nipple 23 to form an interlocking fit. With cover 10 positioned on probe 12 of thermometer 14 as shown in FIG. 1, it will be appreciated that sheath 16 serves as a sanitary barrier. Specifically, sheath 16 acts as a barrier which protects a patient from direct contact with probe 12 and probe tip 28 when these parts of thermometer 14 otherwise would come into physical contact with the patient (not shown). Although sheath 16 is an effective sanitary barrier, infrared radiation from a body surface, such as the inside of the patient's ear canal, can still pass through window 20 of sheath 16 and on through channel 44 of probe 12 for detection and display by thermometer 14.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of that which is patentable.

We claim:

1. A unitary cover for the hollow probe on a radiation detecting thermometer with said probe having a proximal portion at said thermometer and a distal opening at its opposite end, which cover comprises:

a one-piece hollow sheath having a side wall composed of a proximal portion followed by a distal portion, an open end of said proximal portion integral with which is a base engaged therewith for mounting said sheath on said probe and a closed end integral with said distal portion and in use disposed across said distal opening as a window, said closed end and said distal portion being of the same thickness which is substantially thinner than said proximal portion and said base and sufficiently thin to be effectively transparent for transmission of infrared radiation through said distal opening.

2. A cover as defined in claim 1 wherein said proximal portion is frustum-shaped and is made of a polymer material.

3. A cover as defined in claim 1 wherein said probe has an infrared transparent end and said window stretchably covers said end.

4. A cover as defined in claim 1 wherein said side wall connects said window with said base, said wall having a distal portion and a proximal portion with said distal portion and said window having the same thickness, and said proximal portion tapering with increasing thickness from said distal portion in the direction toward said base.

5. A cover as defined in claim 1 wherein said side wall connects said window with said base, said side wall having a distal portion and a proximal portion with said distal portion and said window having a first thickness and said proximal portion having a thickness greater than said first thickness.

6. A cover as defined in claim 5 wherein said base and said proximal portion of said wall are stiff as compared with said distal portion.

7. A cover as defined in claim 5 wherein said window and said distal portion are flaccid as compared with said proximal portion.

8. A cover as defined in claim 1 wherein said base has a configuration that establishes an interference fit with said probe.

9. A unitarily constructed seamless sanitary one-piece cover for the probe on a radiation detecting thermometer with said probe having a proximal portion at said thermometer and a distal opening at its opposite end, which cover comprises:
an effectively IR-transparent window positionable over said distal opening of said probe to close said probe and allow radiation to pass through said probe;
a continuous wall terminating in a distal closed end which constitutes said window beyond which said wall has a distal portion of the same thickness integrally formed with said window and with said wall continuing and becoming thicker only beyond said distal portion as a proximal portion terminating in an open proximal end defining a periphery;
and a base dimensioned for surrounding engagement with said probe, said base being integrally formed with said wall to circumferentially surround said periphery and extend radially therefrom.

10. A cover as defined in claim 9 wherein said proximal portion is frustum-shaped and is made of a polymer material.

11. A cover as defined in claim 9 wherein said distal portion and said window have the same thickness and said proximal portion and said base have a thickness larger than said same thickness, said wall gradually tapering in thickness from said proximal portion to said same thickness of said distal portion and said window.

12. A cover as defined in claim 9 wherein said window stretchably covers said distal opening of said probe.

13. A cover as defined in claim 9 wherein said base and said proximal portion of said wall are substantially stiff as compared with said distal portion.

14. A cover as defined in claim 9 wherein said base has a configuration that establishes an interference fit with said probe.

* * * * *

UNITED STATES PATENT OFFICE
CERTIFICATE OF CORRECTION

Patent No. 5,088,834　　　　　　　　Dated February 18, 1992

Inventor(s) Randal R. Howe and Joseph P. Brown

It is certified that error appears in the above-identified patent and that said Letters Patent is hereby corrected as shown below:

Column 1, line 33: "sterilizable" should read -- sterilized --.

Column 4, line 1: "approximate" should read -- proximate --.

Column 4, line 7: "co-polymer are preferred)." should read -- co-polymer) are preferred. --.

Column 5, line 59: "preferred." should read -- preferred). --.

Signed and Sealed this

Twenty-second Day of June, 1993

Attest:

MICHAEL K. KIRK

Attesting Officer　　Acting Commissioner of Patents and Trademarks